United States Patent [19]

Saitoh et al.

[11] Patent Number: 5,472,951
[45] Date of Patent: Dec. 5, 1995

[54] STABILIZER FOR PHOSPHOLIPID VESICLES

[75] Inventors: Akihisa Saitoh, Togane; Kiyoshi Yoshimura; Takanao Suzuki, both of Chiba; Mikimasa Takisada, Yokohama; Shinji Takeoka, Tokyo; Hiromi Sakai, Tokyo; Eishun Tsuchida, Tokyo, all of Japan

[73] Assignee: Chiba Flour Milling Co., Ltd., Chiba, Japan

[21] Appl. No.: 28,519

[22] Filed: Mar. 9, 1993

[30] Foreign Application Priority Data

| Apr. 21, 1992 | [JP] | Japan | 4-126716 |
| May 18, 1992 | [JP] | Japan | 4-148922 |
| Jun. 26, 1992 | [JP] | Japan | 4-191364 |
| Jul. 10, 1992 | [JP] | Japan | 4-206136 |

[51] Int. Cl.$^6$ .......................... A61K 9/10; A61K 9/127; A61K 9/133; C07H 15/00
[52] U.S. Cl. .......................... 514/54; 424/450; 536/1.11; 536/4.1; 536/17.4; 536/17.9; 536/18.7; 514/23; 514/25
[58] Field of Search .......................... 514/23, 25, 54; 536/1.11, 4.1, 17.4, 17.9, 18.7; 424/450

[56] References Cited

U.S. PATENT DOCUMENTS

| 3,839,318 | 10/1974 | Mansfield | 514/26 |
| 4,614,796 | 9/1986 | Kawamata et al. | 54/26 |
| 4,785,084 | 11/1988 | Warren et al. | 536/17.9 |
| 5,049,388 | 9/1991 | Knight et al. | 424/450 |

FOREIGN PATENT DOCUMENTS

| 0382070 | 8/1990 | European Pat. Off. . |
| 0491960 | 1/1992 | European Pat. Off. . |

OTHER PUBLICATIONS

Chemistry Letters, No. 9, Sep. 1992, Tokyo, JP pp. 1877–1880, Takeoka et al. "Inhibition of intervesicular aggregation of phospholipid vesicles by incorporation of dialkyl . . . ".

*Primary Examiner*—Ronald W. Griffin
*Attorney, Agent, or Firm*—McAulay Fisher Nissen Goldberg & Kiel

[57] ABSTRACT

An oligosaccharide lipid is provided which has 2 to 20 saccharide units, and has a hydrophobic group linked by an ether linkage to an anomer carbon on a reducing end group. A stabilizer for a phospholipid vesicle is also provided which comprises an oligosaccharide derivative having 2 to 20 saccharide units, and having a hydrophobic group linked by an amide linkage or an ether linkage to an anomer carbon on a reducing end group constituted of an aldose.

6 Claims, 1 Drawing Sheet

STABILIZER FOR PHOSPHOLIPID VESICLES

BACKGROUND OF THE INVENTION

1. Field of the Invention

The present invention relates to a novel oligosaccharide lipid which has a definite structure and is useful for stabilizing a phospholipid vesicle (hereinafter simply referred to as a "vesicle"). In the present invention, the oligosaccharide includes disaccharides.

The present invention also relates to a vesicle stabilizer which comprises an oligosaccharide lipid having a definite structure, and is useful for stabilizing a vesicle.

The vesicle stabilizer of the present invention modifies the vesicle, thereby inhibiting aggregation of the vesicles, stabilizing the dispersion of the vesicles against ions and proteins, or extending the half-life of the vesicles in blood stream.

The vesicle which has been modified with the stabilizer of the present invention is useful for drug-delivery systems and controlled drug-releasing systems in which physiologically active substances such as adriamycin and prostaglandin are enclosed in the internal aqueous phase of the vesicle. The modified vesicle which encloses purified hemoglobin is useful as an artificial red blood cell.

2. Description of the Related Art

Vesicles are normally unstable to come to aggregate or fuse together or to cause leakage of encapsulated molecules. A number of reports have been presented to stabilize the vesicles as mentioned below.

Vesicles are stabilized by polymerizing assemblies of phospholipids having an unsaturated groups (for example, see a review: H. Ringsdof, et al.: Angew. Chem., Int. Engl., 27, 113 (1988)). However, the polymerization of the membrane-constituting substance impairs the inherent characteristics such as gel-liquid crystal phase transition, phase separation, and membrane fluidity, causing loss of the functions based on these characteristics.

The vesicle structure of the phospholipid assemblies is stabilized by coating of its surface with carboxymethylchitin (H. Izawa, et al.: Biochim. Biophys. Acta, 855, 243 (1986)), and coating with polysaccharide compounds such as dextran and pullulan having a hydrophobic group such as cholesterol (J. Sunamoto, et al.: J. Biochem., 88, 1219 (1980)). Such a method is liable disadvantageously to induce aggregation of vesicles although the membrane fluidity of the vesicle is not greatly affected.

Vesicles are stabilized to aggregation by introducing of an amphiphilic molecule which is formed by bonding polyethylene glycol to a hydrophilic portion of cholesterol or phosphatidyl ethanolamine, thereby the half-life of the vesicles in blood being extended (T. M. Allen, et al.: Biochim, Biophys. Acta, 1066, 29 (1991).

A compound which is formed by introducing a hydrophobic moiety to a polyethylene glycol base is disclosed as a protein adsorption inhibitor to adsorb proteins to phospholipid vesicles and a vesicle aggregation inhibitor (Japanese Patent Application Laid-Open No. Hei-2-149512). However, the effect is not sufficient yet.

A glycosaminoglycan bonded to phospholipid exhibits cell adhesion inhibiting effect, and is useful as a cancer metastasis inhibitor (Japanese Patent Application Laid-Open No. Hei-4-80202).

A cholesterol derivative having β-aminogalactose-moiety is employed for controlling aggregation of vesicles (P. S. Wu, et al.: Proc. Natl. Acad. Sci., USA, 78, 6211 (1981)). The effect of the derivative is not so high as that expected, and is suggested to depend largely upon the polymerization degree of the saccharide moiety.

A hyaluronic acid derivative is disclosed which stabilizes a vesicle dispersion system (Japanese Patent Application Laid-Open No. Hei 3-47801). The hyaluronic acid derivative does not exhibit sufficient stabilizing effect owing to the non-selective introduction of the acyl group by ester linkage, the effect depending greatly on the introduction sites and the number of the introduced acyl groups. Furthermore, the derivative frequently exhibits impractically high viscosity.

The inventors of the present invention disclosed that introduction of an oligosaccharide-fatty acid ester developed by the inventors into the bimolecular layer of a phospholipid vesicle is highly effective in inhibition of aggregation and fusion of vesicles, namely stabilization of the dispersing state of vesicles (Japanese Patent Application Laid-Open No. Hei 1-294701). Oligosaccharide ester derivatives having a longer saccharide chain give higher effect, and the derivatives based on disaccharides do not give sufficient effect on inhibition of aggregation of vesicles.

The invention disclosed in the above Japanese Patent Application Laid-Open No. Hei 1-294701 improves significantly the stability of vesicles. However, since the oligosaccharide has many reactive hydroxyl groups, the long-chain fatty acid group is introduced non-selectively to the oligosaccharide in a variety of numbers and a variety of sites in the oligosaccharide molecules. Consequently, isolation and purification of the product are complicated, and the yield is low. Moreover, the effect of stabilizing the vesicle dispersion and the fixation of the oligosaccharide-fatty acid ester onto the membrane surface of the vesicle depend disadvantageously on the kind of the isomers of the oligosaccharide, and the correlation of the stabilizing effect to the structure of the isomers is not clear.

The present invention intends to solve the above problems.

SUMMARY OF THE INVENTION

The present invention intends to provide an oligosaccharide lipid having a definite structure which is prepared by introducing a hydrophobic group selectively to the anomer carbon of an oligosaccharide.

The present invention further intends to provide a stabilizer for phospholipid vesicles comprising the above oligosaccharide derivative.

The present invention provides an oligosaccharide lipid having 2 to 20 saccharide units, and having a hydrophobic group linked by an ether linkage to an anomer carbon on a reducing end group.

The present invention also provides a stabilizer for phospholipid vesicles comprising an oligosaccharide lipid having 2 to 20 saccharide units, and having a hydrophobic group linked by an amide linkage to an anomer carbon on a reducing end group constituted of an aldose.

The present invention further provides a stabilizer for phospholipid vesicles comprising an oligosaccharide lipid having 2 to 20 saccharide units, and having a hydrophobic group linked by an ether linkage to an anomer carbon on a reducing end group.

DETAILED DESCRIPTION OF THE PREFERRED EMBODIMENT

Figure 1:
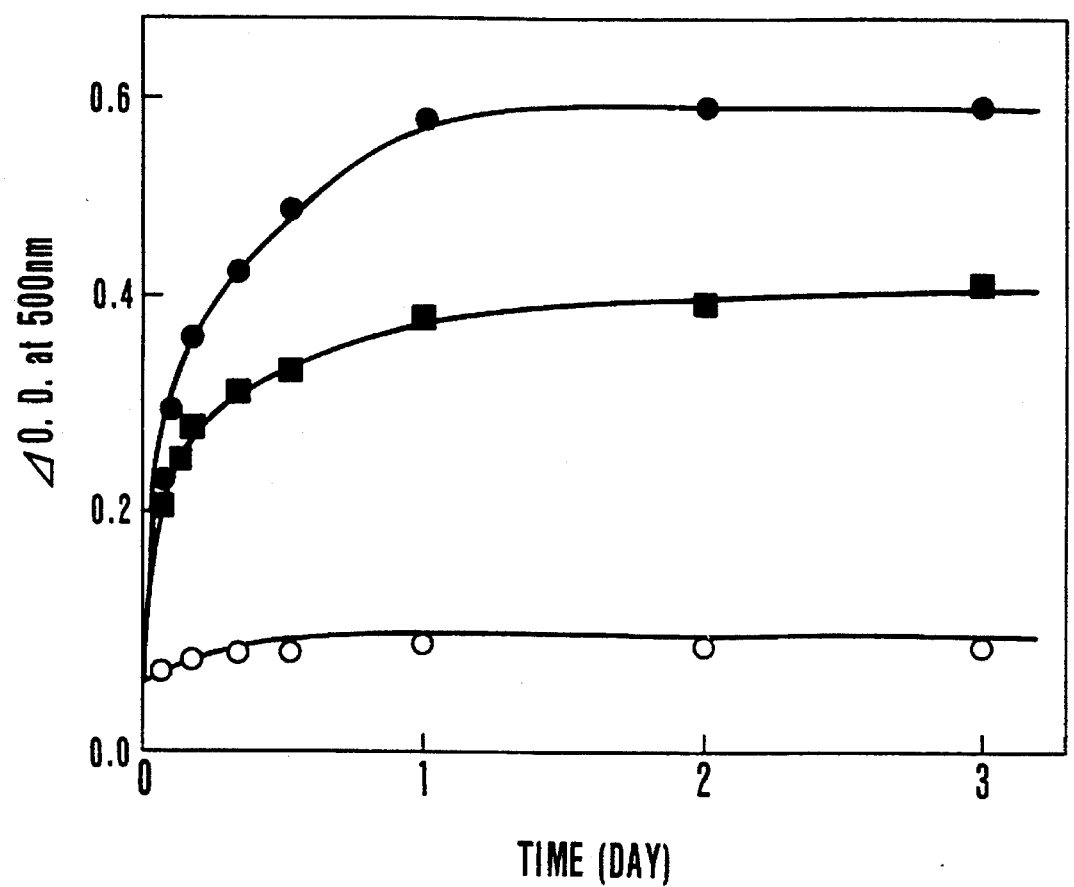
FIG. 1 shows the change with time of turbidity at 500 nm of a 0.5 wt % dispersion of dipalmitoylphosphatidylcholine vesicles stabilized by an oligosaccharide of the present invention, when the vesicles are left standing at room temperature.

The oligosaccharide as the vesicle stabilizer of the present invention needs to have well-adjusted hydrophilic-hydrophobic balance. Therefore, the oligosaccharides are selected which have 2 to 20 monosaccharide units (the number of saccharide units of 2 to 20) and have an aldose group as the reducing end group, such as maltopentaose. The oligosaccharides of the present invention include sugar alcohols of the oligosaccharides.

The oligosaccharides of the number of saccharide units of 2 to 20 can be fractionated according to the number and the kinds thereof in high purity by gel filtration through a temperature-controlled column. A differential refractometer is used for the detection thereof. The qualitative identification and the purity determination of the fractionated oligosaccharide can be conducted by use of a silica gel thin plate by multidevelopment with a mixed solvent (composed of 1-butanol, pyridine, and water) and color-development by sulfuric acid, or otherwise by liquid chromatography employing an amino column and a mixed solvent (composed of acetonitrile and water). The oligosaccharide used in the present invention may be a commercial pure product, provided that its structure is definite.

The hydrophobic compound having a hydroxyl group for forming the oligosaccharide ether derivative of the present invention has an alkyl chain of preferably 12 to 22 carbons in order to obtain satisfactory hydrophilic-hydrophobic balance, and if it is unsaturated, the number of the unsaturation is preferably 1 to 4. The same hydrophobic compound is selected for the oligosaccharide ether derivative for the stabilizer.

The hydrophobic compound having a hydroxyl group employed in the present invention includes primary alcohols and secondary alcohols which have an alkyl group of 12 to 22 carbons such as lauryl alcohol, cetyl alcohol, stearyl alcohol, and behenyl alcohol as linear primary alcohols. The hydrophobic compound also includes linear primary unsaturated alcohols, branched primary saturated alcohols, branched primary unsaturated alcohols, secondary saturated alcohols, and secondary unsaturated alcohols such as 1-dodecenol-1, oleyl alcohol, linolenyl alcohol, and the like. The hydrophobic compound further includes dialkylglycerols having saturated or unsaturated long carbon chains at 1- and 3-carbons or 1- and 2-carbons of glycerol; and sterols such as cholesterol, cholestanol, sitosterol, and ergosterol.

The hydrophobic group is introduced to the anomer carbon of the end of the saccharide chain by ether linkage according to the principle of the method of Ogawa, et al. of bonding a dialkylglycerol to an anomer carbon at the end of a disaccharide (T. Ogawa, et al., Carbohydrate Res. 98, C6 (1981); T. Ogawa, et al., Agric. Biol. Chem., 45 (10), 2392 (1981); and T. Ogawa, et al., Agric. Biol. Chem., 46 (1), 255 (1982). The introduction of the hydrophobic group is described below specifically.

Firstly, the hydroxyl groups of the oligosaccharide are protected by acetylation. For this purpose, distilled pyridine is added to the oligosaccharide, and then acetic anhydride is added thereto dropwise under ice cooling. The reaction mixture is left standing overnight at 4° C. The product is recrystallized from isopropyl alcohol to obtain an acetylated oligosaccharide. Then a hydrophobic group is introduced by ether linkage to the anomer carbon at the end of the saccharide chain. Therefor, the aforementioned hydrophobic compound having a hydroxyl group is made to react with the above acetylated oligosaccharide with a catalyst of trimethylsilyltrifluoromethanesulfonic acid in dichloroethane in the presence of powdery molecular sieve 4A.

Before deprotection to obtain the intended oligosaccharide derivative, the acetylated oligosaccharide needs to be purified sufficiently. Therefor, the obtained acetylated product is purified by liquid chromatography employing silica gel and a mixed solvent of toluene and ethyl acetate. The fractions are identified by Fourier transform nucleomagnetic resonance (hereinafter referred to as "NMR"), or infrared absorption spectroscopy (hereinafter referred to "IR"). Incidentally, the separation and the purification of acetylated oligosaccharide derivative may be conducted by any of other methods such as supercritical chromatography, reversed phase type column, solvent extraction, and the like.

Finally, to eliminate the acetyl groups, a basic substance such as aqueous ammonia and triethylamine is added to the acetylated oligosaccharide derivative in a mixed solvent of methanol with water, and the mixture is refluxed for more than 12 hours. The resulting product is recrystallized twice or more from a polar solvent such as methanol to obtain the final product of the oligosaccharide derivative for the stabilizer for a phospholipid vesicle of the present invention.

The oligosaccharide lipid can be identified by proton-NMR, carbon-NMR, or IR. The purity of the oligosaccharide lipid having an ether linkage obtained as above is determined by silica gel-based thin layer chromatography, or high speed liquid chromatography.

On the other hand, the oligosaccharide lipid having amide linkage for the vesicle stabilizer of the present invention employs a compound having a primary amino group, namely an amine, for the hydrophobic group introduction to the anomer carbon by amide linkage. The amine includes aliphatic primary amines having 12 to 22 carbons which may have 1 to 4 unsaturated bonds such as laurylamine, cetylamine, stearylamine, behenylamine, and oleylamine; and also includes phospholipids such as phosphatidylethanolamine, and phosphatidylserine.

The introduction of the hydrophobic group to the anomer carbon by amide linkage at the end of the saccharide chain is conducted as described below specifically.

The reducing end group of the oligosaccharide is oxidized by hypoiodous acid to open the ring at the anomer carbon to form a carboxylic acid salt, and the reaction mixture is treated with cation-exchange column to change the carboxylic acid salt to a carboxylic acid. The obtained oligosaccharide was precipitated from ethanol and washed with acetone. This carboxylic acid is dehydrated by heating at 40° C. for 24 hours in vacuo to form a lactone ring with the reducing end group.

The product is dissolved in methanol, formamide, or dimethylformamide. Thereto, a solution of an aliphatic primary amine or a phospholipid having a primary amino group in methanol or chloroform is added to form a uniform solution. The mixed solution is allowed to react at a temperature of from 40° to 80° to obtain the intended oligosaccharide lipid. The obtained oligosaccharide lipid is purified by washing with water and hexane, and by treatment by a reversed phase type silica gel column and a normal phase type silica gel column.

The reaction of introduction of the hydrophobic group to the anomer carbon at the end of the saccharide chain by amide linkage is readily practiced, provided that the oligosaccharide has 2 to 20 saccharide units and has a reducing end group of an aldose.

The purity of the oligosaccharide derivative having an amide linkage obtained as above can be determined by silica gel-based thin layer chromatography or high speed liquid chromatography.

The stability of the vesicles stabilized by the stabilizer of the present invention is confirmed as described below. To phospholipids or mixtures of phospholipids and steroids such as cholesterol, cholestanol, etc. or mixtures of phospholipid, steroids, and negatively-charged lipids such as stearic acid, dicetyl phosphate, etc., the stabilizer of the present invention is added in an amount of 0.01 mol % or more, preferably 0.05 mol % or more. The mixture is dispersed by an ultrasonicator, a microfluidizer, an extruder, or any known means to prepare a dispersion of vesicles in particle size of from 50 to 200 nm. The particle size of the vesicle is measured by a particle size analyzer, or transmission electron microscopic observation of negatively stained vesicles.

The ratio of introduction of the stabilizer into the vesicles is determined by treating the dispersion of the vesicles by gel filtration or ultracentrifuge to remove the superfluous stabilizer which has not been introduced into the vesicles, and quantitatively determining saccharide in respective fractions by a phenol-sulfuric acid method. The stabilizer of the present invention, when employed in an amount of from 2 to 10 mol %, is introduced into the vesicles in a ratio of 90% or more.

The dispersion stability of the vesicle is evaluated by measuring the change with time of the absorbance (turbidity) with a spectrophotometer at a wavelength of 500 to 800 nm of the gel-filtered dispersion which is left standing at room temperature. Otherwise, the dispersion stability of the vesicle can be measured by the viscosity of the vesicle dispersion with a rotating viscometer, or microscopic observation by electron microscopy.

The stabilizer of the present invention has a definite structure, and is suitable for modifier of a vesicle because of its excellent affinity to the phospholipid. The stabilizer introduced into the vesicle has its saccharose structure portion exposed to the aqueous phase to distribute uniformly on the membrane of the vesicle.

The stabilizer of the present invention is capable of inhibiting the leakage of the encapsulated molecules to the outside of the vesicle, and further is useful for various purposes such as inhibition of parent cell formation, prevention of vesicle aggregation, prevention of membrane fusion, labelling for recognition by a specific antibody, inhibition of phagocytosis, and so forth. Furthermore, the vesicle stabilizer of the present invention causes little increase in the viscosity of the modified vesicle dispersion.

When a carrier comprising vesicles containing functional molecules in an internal aqueous phase thereof is dosed to a living body, the vesicles usually come to aggregate under the action of water-soluble proteins, calcium ion, or the like in the serum, and the carrier is excluded from the blood stream in a short time by enclosure by a reticuloendothelial system or a phagocyte.

On the contrary, the stabilizer of the present invention enables the control of the half-life in blood stream by modification of the vesicle surface.

The stabilizer of the presnet invention is applicable to modification of any vesicles: not only to vesicles constructed from a known saturated phospholipid but also vesicles constructed from a copolymerized phospholipid.

Furthermore, the stabilizer can be more effectively used for stabilization by copolymerization thereof with a polymerizable phospholipid in the bimolecular layer of the vesicles.

The combined use of the vesicle stabilizer with a polymerizable phospholipid is useful, further for example, for improvement of culture efficiency by application and copolymerization of the combined mixture on a surface of cultivation vessel to make the surface hydrophilic and to give the surface the high affinity to cells.

The present invention is described below in more detail with reference to examples.

EXAMPLE 1

Into 15 ml of distilled pyridine, was added 2 g of maltopentaose. Thereto 15 ml of distilled acetic anhydride was gradually added dropwise at 4° C. The reaction mixture was further stirred at 4° C. for 12 hours. Then the solvent was replaced by chloroform, and the chloroform layer was washed with aqueous dilute sodium hydrogencarbonate solution. The chloroform was evaporated off, and the crude product was recrystallized twice from 2-propanol to obtain an acetylated maltopentaose in a yield of 2.58 g (yield: 69%).

The completion of the reaction was confirmed by IR spectrum (NaCl) by disappearance of the absorption peak at about 3500 $cm^{-1}$ assigned to the hydroxyl group and appearance of an absorption peak at 1750 $cm^{-1}$ assigned to the ester linkage. The progress of the reaction was also confirmed by proton NMR (solvent: $CDCl_3$) from the fact that the found proton integral ratio of 1.50 for the acetyl group (1.8 to 2.3 ppm) to the saccharide skeleton (3.4 to 5.7 ppm) in comparison with the theoretical value thereof of 1.46. In silica gel thin chromatography (hereinafter referred to "TLC"), the product gave two spots (Rf=0.40 and 0.15, solvent; toluene:ethyl acetate=1:4 by volume), which are ascribable to the optically active isomers at the anomer carbon, and separation by difference of the polarity of the α-isomer and the β-isomer. The two isomers were used in the subsequent reaction without separation.

2.0 g of the acetylated maltopentaose and 0.78 g of 1,2-dioctadecyl glycerol (in equivalent moles) were dissolved in 45 ml of dichloroethane in the presence of 12 g of powdery molecular sieve 4A. Thereto 1.5 ml of trimethyl-silyltrichlorometnanesulfonic acid was added dropwise, and the mixture was stirred at room temperature for 65 hours. Then the mixture was filtered, concentrated, and purified through silica gel column (solvent; toluene:ethyl acetate=1:1 by volume) to obtain the acetylated product of the oligosaccharide of the present invention.

The obtained acetylated oligosaccharide lipid gave two spots in TLC analysis (Rf=0.43, and 0.22, solvent; toluene:ethyl acetate=3:1 by volume). The one of higher Rf, the α-isomer, was obtained in a yield of 150 mg, and the other one of lower Rf, the β-isomer was obtained in a yield of 460 mg. The overall yield rate was 23%.

The progress of the intended reaction was confirmed by IR spectrum and proton NMR (solvent; $CDCl_3$). In the IR spectrum, an absorption peak assigned to a long alkyl chain was observed at the region of 2700 to 2900 $cm^{-1}$. In proton NMR, the proton integral ratio of an alkyl group (0.7 to 1.7 ppm) to an acetyl group (1.9 to 2.3 ppm) was found to be 1.48 in comparison with the theoretical value thereof of 1.46.

The deacetylation of the acetylated product of the oligosaccharide lipid of the present invention was conducted as follows. The α- or β-isomer was dissolved in methanol, a small amount of triethylamine and water were added thereto, and the mixture was refluxed for 12 hours. Then the reaction mixture was cooled to 0° C., and the crude product was recrystallized to recover the deacetylated oligosaccharide lipid of the present invention in a yield of 69%. The deacetylation was confirmed by appearance of an absorption peak assigned to a hydroxyl group at about 3500 cm$^{-1}$ and disappearance of the absorption peak assigned to a carbonyl group at about 1750 cm$^{-1}$ in IR spectrometry.

The introduction ratio of the glycerol to the saccharide chain of 1:1 was confirmed by proton NMR spectrum. In the NMR spectrum, the proton integral ratio of —CH$_3$ (δ: 0.7–1.0) and —(CH$_2$)$_{16}$— (δ: 1.1–1.2) to the saccharide skeleton, glycerol, and —OCH$_2$CH$_2$ (δ: 2.8–6.6) was found to be 1.13 in comparison with the theoretical value of 1.17. ("δ" means chemical shift (ppm).)

The α-isomer and β-isomer of the oligosaccharide derivative of the present invention gave respectively a single spot in TLC (solvent; chloroform:methanol=2:1 by volume) with Rf values of 0.10 for the α-isomer and 0.16 for the β-isomer. In carbon NMR (solvent; dimethylsulfoxide), the chemical shift of the terminal anomer carbon for maltopentaose moved from 92 ppm to 103 ppm, thereby the selective introduction of dialkyl glycerol to the terminal anomer carbon being confirmed.

Accordingly, the oligosaccharide lipid of the present invention in this Example was maltopentaose distearyl glycerol (hereinafter referred to as "MPDSG") having definite structure.

The ability of the oligosaccharide lipid of the present invention, namely of MPDSG, for stabilizing a vesicle was evaluated as follows. 3 mg of MPDSG and 100 mg of dipalmitoyl phosphatidylcholine (hereinafter referred to as "DPPC") as a phospholipid were dissolved in methanol. The methanol was evaporated by use of a rotary evaporator to form a thin film on the inside wall of an eggplant shape flask. Thereto, 5 ml of pure water and several glass beads were added, and the content of the flask was agitated at 60° C. by means of a vortex mixer to form a whitish turbid liquid. This whitish turbid liquid was treated with an extruder. In the treatment, the pore diameter of the filters made of polycarbonate were changed sequentially in the sizes of 0.4 μm, 0.2 μm, 0.1 μm, and 0.05 μm, and the liquid was passed through each of the filters five times to obtain a whitish transparent DPPC vesicle dispersion. The obtained vesicles had average diameters of 57±12 nm and 55±10 nm according to measurement with a particle size analyzer and a transmission electron microscope with negative stain respectively.

The introduction ratio of the MPDSG into the vesicle was determined by diluting the above vesicle dispersion to 0.5% by weight, subjecting the dispersion to gel filtration (Sepharose CL-4B, 20 nmd×300 nmh, made by Pharmacia Co.) to remove MPDSG not introduced into the bimolecular layer of the vesicle from the system, and determining the saccharide in the respective fractions by a phenol-sulfuric acid method. It was found that 99% of the added MPDSG had been taken into the vesicle. The stability of the vesicle dispersion which had been passed through the 0.05 μm filter was evaluated by measuring the change of absorbance (turbidity) at 500 nm with time on standing at room temperature by means of a UV-visible light spectrophotometer.

FIG. 1 shows the change with time of the turbidity (at 500 nm) of the MPDSG-modified vesicle dispersion (indicated by blank circles), a sugar ester-modified vesicle dispersion (indicated by solid squares), and an unmodified DPPC vesicle dispersion (indicated by solid circles) at a concentration of 0.5% by weight on standing at room temperature. As shown in FIG. 1, the unmodified DPPC vesicles came to aggregate immediately, as indicated by rise of the turbidity of the dispersion, when the sample just prepared was left standing at room temperature. The sugar ester-modified vesicle dispersion exhibited turbidity rise of 70% in comparison with that of the unmodified vesicle, the aggregation not being sufficiently inhibited. On the other hand, the dispersion of the vesicle modified with the oligosaccharide lipid of the present invention, namely MPDSG, exhibited turbidity rise of about 7% of that of the unmodified system in a short time after preparation and subsequent standing, but little turbidity increase later, showing the inhibition of the aggregation.

As shown above, the MPDSG of the present invention exhibited great effect of stabilizing a dispersion of vesicles.

EXAMPLE 2

An acetylated laminaripentaose prepared by acetylating 2 g of laminaripentaose in the same manner as in Example 1 was reacted with an equimolar amount stearyl alcohol and was purified in the same manner as in Example 1 to obtain acetylated laminaripentaose monostearyl ether in a yield of 1.5 g (overall % yield: 40%). The obtained product exhibited an absorption peak assigned to the long chain alkyl at the region of 2700 to 2900 cm$^{-1}$ in IR spectrum. The product gave, in proton NMR (solvent; chloroform), the proton integral ratio of alkyl (0.7–1.7 ppm) to acetyl (1.9–2.3 ppm) of 0.80 in comparison with the theoretical value of 0.73, thereby the progress of the etherification being confirmed. The product was deacetylated and recrystallized to recover laminaripentaose monostearyl ether (hereinafter referred to as "LPMS"), an oligosaccharide derivative of the present invention, in a yield of 80%.

The completion of the deacetylation in the preparation of LPMS of the present invention was confirmed by IR spectrum. The introduction of stearyl alcohol to the saccharide chain in a ratio of 1:1 was confirmed by proton NMR spectrum in which the proton integral ratio of —CH$_3$ and —(CH$_2$)$_{16}$— to the saccharide skeleton and —OCH$_2$CH$_2$ (δ: 2.8–5.6) was found to be 1.46 in comparison with the theoretical value of 1.51.

The effect of the LPMS of the present invention on stabilization of vesicles was evaluated as follows. A powdery lipid mixture containing LPMS was prepared from dimyristoyl phosphatidylcholine, cholesterol, myristic acid, and LPMS (in molar ratio of 7:7:2:0.3) was prepared by freeze-drying. 100 ml of saline was added to 10 g of the above powdery lipid mixture, and the mixture was stirred at 4° C. for 24 hours to prepare a liquid dispersion. This dispersion was treated with a microfluidizer at a pressure of 4500 psi at 4° C. for 10 minutes to prepare a dispersion of vesicles having an average diameter of 300±130 nm. The introduction ratio of the LPMS was 85% according to saccharide determination of the supernatant liquid after centrifugation.

The precipitation of the vesicles was dispersed again to be 5 wt %, and thereto dextran (molecular weight of 40000) was added as a colloid osmotic pressure controller. The stability of the dispersion was observed by determination of turbidity at 800 nm. The unmodified vesicles gave turbidity increase by addition of dextran in an amount of only 1% by weight, causing remarkable aggregation, whereas the LPMS-modified vesicles did not give turbidity increase, exhibiting an strong effect of inhibiting aggregation of dextran.

EXAMPLE 3

500 mg of a powdery lipid mixture containing MPDSG of the present invention was prepared from DPPC, cholesterol, distearyl phosphatidic acid, and MPDSG (in molar ratio of 10:9:0.9:0.5) was prepared by freeze-drying from benzene. Thereto 10 ml of physiological saline was added, and the mixture was stirred at 4° C. for 12 hours to prepare a dispersion of mixed lipids. This dispersion was treated with an extruder to pass finally a filter of which pore diameter was 0.2 μm, and to obtain a dispersion of vesicles having an average particle diameter of 200 nm. The introduction ratio of the MPDSG was 98%.

The stability of the vesicles was evaluated as below. The precipitate of the vesicles prepared by centrifuge was dispersed again into saline by a vortex mixer. To this sample, calcium chloride (as calcium ion) was added to be 5 mM, and the viscosity of the dispersion was measured with a rotating viscometer (Vismetron VS-AK). The viscosity of 5 cp was not changed by addition of the calcium ion. Thus, MPDSG of the present invention inhibited nearly completely the aggregation of the vesicles even when calcium ion was added to the vesicle liquid dispersion, whereas the unmodified vesicles containing no MPDSG caused remarkable rise of the viscosity on addition of calcium ion, showing occurrence of aggregation.

EXAMPLE 4

10.0 g of a powdery lipid mixture containing the MPDSG of the present invention (hydrogenated lecithin: cholesterol:palmitic acid:MPDSG=7:7:2:0.4 in molar ratio) was dispersed in 200 ml of 40% stroma-free hemoglobin solution. The dispersion was stirred at 4° C. for 2 hours, and treated with a microfluidizer to obtain a dispersion of vesicles having an average diameter of 300±98 nm. This dispersion was passed through a filter of 0.2 μm diameter by an extrusion method, and hemoglobin and not-introduced MPDSG in the external aqueous phase are removed by gel filtration to obtain a dispersion of vesicles having an average particle diameter of 203±50 nm and enclosing hemoglobin.

The hemolysis inhibition activity of the vesicle against washed human RBC (red blood cell) was observed as follows. The obtained dispersion of the hemoglobin-enclosing vesicles was adjusted to have a pH value of 7.4. Thereto human RBC was added to 0.5% by weight. The mixture was incubated at 37° C. for 2 hours, and was subjected to centrifuge at 5000 G for 30 minutes. The action of the vesicle on hemolysis was observed by determination of the hemoglobin in the supernatant liquid. As the results, in the system having no MPDSG, hemolysis of 90% was observed, whereas in the system having MPDSG of the present invention, hemolysis of only 5% was observed, which shows the remarkable hemolysis-inhibiting effect of the MPDSG of the present invention.

The hemoglobin-enclosing vesicle dispersion was adjusted to have a lipid concentration of 5% by weight, a hemoglobin concentration of 7% by weight, and pH of 7.4. The liquid dispersion was dosed to rat tail veins of a group of rate in an amount of 4000 mg/kg. The half-life of the hemoglobin-enclosing vesicles from the blood stream was analyzed by drawing the blood and separating the red blood cells from the hemoglobin-enclosing vesicles. As the results, the average half-life of the system containing vesicles modified by MPDSG, an oligosaccharide derivative of the present invention, and that of the unmodified system were respectively 38 hours and 24 hours, which shows the effectiveness of the modification of the vesicle with MPDSG.

EXAMPLE 5

In 50 ml of methanol kept at 40° C., 3.06 g of iodine was dissolved, and thereto was added an aqueous solution of 5.0 g of maltopentaose in 5 ml of water. The mixture was stirred at 40° C. for 60 minutes. Thereto 4% potassium hydroxide solution in methanol was added until the color of the iodine disappeared to obtain crystalline precipitate. The crystalline precipitate was washed with methanol, ethanol, and ether. In this stage the ring at the anomer carbon of the maltopentaose is opened in a form of carboxylic acid salt of potassium.

The aqueous solution of the resulting crystalline matter was treated with a cation-exchange resin, Amberlite IR-120B, to convert the salt to the carboxylic acid. The oligosaccharide was precipitated from ethanol and washed with acetone (methanol may be used in place of the ethanol). Then the carboxylic acid was dehydrated by heating at 40° C. for 24 hours in vacuo to cause ring closure to convert the reducing terminal group of the maltopentaose into a lactone ring. The yield of the maltopentaose lactone was 2.70 g (54%).

1.00 g of the maltopentaose lactone was dissolved in 10 ml of refluxing methanol. Thereto, a solution of 0.29 g of cetylamine in 30 ml of methanol was added, and the mixture was refluxed for 4 hours to introduce the cetylamine to maltopentaose by amide linkage to obtain a crude product of maltopentaose cetyl amide (hereinafter referred to as "MPCA").

The obtained MPCA was dried at 40° C. under reduced pressure for 15 hours, and then it was washed with pure water, and hexane. The MPCA was again dissolved in methanol, and was purified by Licroprep RP-18 column. The yield of the resulting MPCA was 0.53 g (41%).

The modification of the vesicle was conducted as follows. 7.3 mg of the obtained MPCA was dissolved in 1 ml of methanol. Thereto, a solution of 100 mg of dipalmitoyl phosphatidyl choline (DPPC) in 5 ml of methanol was added, thereby MPCA being about 5 mol % relative to DPPC. With this mixture, a thin film was formed on an inside wall of an eggplant shape flask by means of a rotary evaporator. Thereto, 5 ml of pure water was added, and the mixture was agitated by a probe type ultrasonicator to obtain a white translucent dispersion of MPCA-modified vesicles. Having been kept standing at 50° C. for 2 hours, this liquid dispersion was subjected to measurement of the particle diameter of the vesicle with a particle size analyzer measurement apparatus. The average diameter was 32±7 nm.

The dispersion stability of the MPCA-modified vesicle was evaluated by leaving the dispersion at 25° C. for 3 days and measuring the change of the absorbance (turbidity) at 500 nm. Consequently, little rise in turbidity was observed. On the other hand, the unmodified DPPC vesicle dispersion prepared in the same manner exhibited increase of turbidity immediately after standing at 25° C., showing aggregation of the vesicles. The turbidity increase at 25° C. for three days of the MPCA-modified vesicle dispersion was only 6.3% relative to that of the unmodified DPPC vesicle dispersion taken as 100%.

The above results are shown in Table 1 together with the results of Comparative Examples 1 to 6 described later. Table 1 shows the relative values of the turbidity increase of DPPC vesicle dispersions at a concentration of 5% by weight during standing at 25° C. for 3 days immediately after the preparation of the vesicle dispersions, where the turbidity increase rate (referred simply to as "increase rate" in Table 1) of unmodified vesicle dispersion is taken to be 100%. The smaller value means the higher stability. Table 1 shows high usefulness of the vesicle stabilizer of the present invention.

TABLE 1

| Modifier | | | Increase rate (%) |
|---|---|---|---|
| Unmodified (DPPC vesicle) | | — | 100 |
| Present invention (Example 5) | | MPCA | 6.3 |
| Comparative Example | | | |
| 1 | Oligosaccharide fatty acid ester | MPMP | 12.7 |
| 2 | Oligosaccharide fatty acid ester | MPDP | 65.4 |
| 3 | Sucrose fatty acid ester | P-1695 | 69.8 |
| 4 | Polyethylene glycol derivative | Nonion S-215 | 49.2 |
| 5 | Polyethylene glycol derivative | Nonion S-220 | 38.1 |
| 6 | Polyethylene glycol derivative | Nonion P-208 | 62.1 |

COMPARATIVE EXAMPLE 1

Maltopentaose monopalmitate (hereinafter referred to as "MPMP") was introduced into a DPPC vesicle under the same conditions and at the same molar ratio as in Example 5. The resulting MPMP-modified DPPC vesicles had an average particle diameter of 34±12 nm, and exhibited the turbidity increase of 12.7% of that of the unmodified DPPC vesicles.

COMPARATIVE EXAMPLE 2

Maltopentaose dipalmitate (hereinafter referred to as "MPDP") was introduced into a DPPC vesicle in the same manner as in Comparative Example 1. The resulting MPMP-modified DPPC vesicles had an average particle diameter of 38±8 nm, and caused the turbidity increase of 65.4% of that of the unmodified DPPC vesicles.

In Comparative Examples 1 and 2, an oligosaccharide fatty acid ester was used as the modifier.

COMPARATIVE EXAMPLE 3

Comparative test was conducted by using a sugar fatty acid ester (P-1695, trada name, made by Mitsubishi Kasei Shokuhin K. K.) as the DPPC vesicle modifier in the same manner as in Example 5. The resulting modified vesicles had an average particle diameter of 27±13 nm, and caused the turbidity increase of 69.8% of that of the unmodified DPPC vesicles, the aggregation inhibiting effect being insufficient.

COMPARATIVE EXAMPLE 4

Comparative test was conducted by using a purified commercial polyethylene glycol monostearyl ether of ethylene glycol polymerization degree of 15 (Nonion S-215, trade name, made by Nippon Oil and Fats Co., Ltd.) as the DPPC vesicle modifier. The resulting modified vesicles had an average particle diameter of 30±11 nm, and caused the turbidity increase of 49.2% of that of the unmodified DPPC vesicles.

COMPARATIVE EXAMPLE 5

Comparative test was conducted by using a purified commercial polyethylene glycol monostearyl ether of ethylene glycol polymerization degree of 20 (Nonion S-220, trade name, made by Nippon Oil and Fats Co., Ltd) as the DPPC vesicle modifier. The resulting modified vesicles had an average particle diameter of 32±12 nm, and caused the turbidity incraes of 38.1% of that of the unmodified DPPC vesicles.

COMPARATIVE EXAMPLE 6

Comparative test was conducted by using a purified commercial polyethylene glycol monocetyl ether of ethylene glycol polymerization degree of 8 (Nonion S-208, trade name, made by Nippon Oil and Fats Co., Ltd.) as the DPPC vesicle modifier. The resulting modified vesicles had an average particle diameter of 33±10 nm, and caused the turbidity increase of 62.1% of that of the unmodified DPPC vesicles.

EXAMPLE 6

Isomaltohexose stearylamide (hereinafter referred to a "IHSA"), a vesicle stabilitzer of the present invention, was prepared according to the method of Example 5. A powdery lipid mixture containing the IHSA (DPPC:cholesterol:distearylphosphatidic acid:IHSA=10:9:0.9:0.5 in molar ratio) was prepared by freeze-drying from benzene. To 500 mg of this freeze-dried mixture, 10 ml of saline was added, and the mixture was stirred at 4° for 12 hours. The resulting white turbid dispersion was treated with an extruder. In this treatment, the dispersion was passed five times through filters of pores diameters of 1.0 μm, 0.4 μm, and 0.2 μm respectively sequentially. Thereby a white transparent IHSA-modified vesicle dispersion was obtained, which had an average particle diameter of 200 nm.

To this dispersion, calcium chloride (as calcium ion) was added to be 5 mM, and the viscosity of the dispersion was measured with a rotating viscometer (Vismetron VS-AK). The viscosity of 5 cp was not changed at all by addition of the calcium ion. Thus the vehicle stabilizer IHSA of the present invention inhibited nearly completely the aggregation of the vesicles even when calcium ion was added to the vesicle dispersion, whereas the dispersion of the vesicles not modified by IHSA aggregated immediately on addition of calcium ion, and the viscosity rose up to 11 cp.

EXAMPLE 7

Maltopentaose distearoyl phosphatidyl ethanolamide (hereinafter referred to a "MPDSPE"), a vesicle stabilizer of the present invention, was prepared according to the method of Example 5. 10.0 g of a powdery mixture containing the MPDSPE (hydrogenated lecithin:cholesterol:stearic acid:MPDSPE=7:7:2:0.4 in molar ratio) was prepared according to the method of Example 5. 10.0 g of this powdery mixture, was dispersed in saline, and stirred at 4° C. for 24 hours. The dispersion was treated by a microfluidizer at 2500 psi, at 4° C. for 15 minutes to obtain vesicles having an average particle diameter of 320±115 nm. This vesicle dispersion was subjected to ultracentrifuge, and the vesicles were separated as precipitate. The precipitate was dispersed again in saline.

The stability of the MPDSPE-modified vesicle was evaluated by adding, to the above dispersion, dextran (molecular weight: 4000) which is a colloid osmotic pressure controller, and measuring the turbidity from the absorbance at 800 nm. As the result, the MPDSPE-modified vesicle dispersion did not show turbidity rise on addition of dextran, whereas a dispersion of vesicles not modified with the MPDSPE gave turbidity rise caused by dextran addition of as small as 1% by weight. This proves the aggregation inhibition effect of the MPDSPE of the vesicle stabilizer of the present invention.

EXAMPLE 8

In 50 ml of methanol kept at 40° C., 5.20 g of iodine was dissolved, and thereto was added an aqueous solution of 3.50 g of maltose in 10 ml of pure water. The mixture was stirred at 40° C. for 30 minutes. Thereto 4% potassium hydroxide solution in methanol was added until the color of the iodine disappeared to obtain crystalline precipitate. The crystalline precipitate was collected by filtration with a glass filter (G4), and was washed with methanol, ethanol, and ether. The ring at the anomer carbon of the maltose was confirmed to be opened in a form of carboxylic acid salt of potassium from appearance of the absorption peak at about 1650 cm$^{-1}$ assigned to carboxylic acid salt by IR spectrometry.

The aqueous solution of the resulting crystalline matter was treated with a cation-exchange resin, Amberlite I-120B, to convert the salt to the carboxylic acid. The saccharide was precipitated from ethanol and washed with acetone (methanol may be used in place of the ethanol). Then the carboxylic acid was dehydrated by heating at 40° C. for 24 hours in vacuo to cause ring closure to convert the carboxylic acid into a maltose lactone. The formation of a lactone ring was confirmed by disappearance of the peak at about 1650 cm$^{-1}$ and appearance of a peak at about 1740 cm$^{-1}$ assignable to C=O stretching vibration of the saccharide skeleton. The yield of the maltose lactone was 2.52 g (72.3%).

2.00 g of the obtained maltose lactone was dissolved in 20 ml of refluxing methanol. Thereto, a solution of 1.45 g of cetylamine in 50 ml of methanol was added, and the mixture was refluxed for 3 hours to introduce the cetylamine to maltose by amide linkage to obtain a crude product of maltose cetyl amide (hereinafter referred to as "MCA").

The obtained MCA was dried at 40° C. under reduced pressure for 16 hours. It was extracted with hexane by solid-liquid extraction to remove impurity into hexane. The MCA after the extraction was again dissolved in methanol, and was purified by liquid chromatography with a Licroprep RP-18 column (any octadecyl-modified column may be used) and a mobile phase of a methanol/pure water mixture to remove unreacted matters. The yield of the purified MCA was 1.91 g (56.9%).

The purified MCA was identified by HPLC analysis by use of a Capcell Pack C18 column (mobile phase: aqueous 95% methanol, flow rate: 0.5 ml/min). Only one fraction of RT value of 20.67 minutes was observed. In IR spectrometry, a peak assigned to an alkyl chain was observed at about 2800 to about 2950 cm$^{-1}$, a peak assigned to C=O stretching vibration of the amide was observed at about 1650 cm$^{-1}$, and a peak assigned to bending vibration of N-H was observed at about 1550 cm$^{-1}$. Accordingly, the obtained MCA had a cetyl group linked through an amide linkage to the anomer carbon of the reducing terminal of maltose.

The modification of the vesicle was conducted as follows. 3.96 mg of the obtained purified MCA was dissolved in 1 ml of methanol. Thereto, a solution of 100 mg of dipalmitoyl phosphatidylcholine (DPPC) in 5 ml of methanol was added, thereby MCA being about 5 mol % relative to DPPC. With this mixture, a thin film was formed on an inside wall of an eggplant shape flask by means of a rotary evaporator. Thereto, 5 ml of pure water was added, and the mixture was agitated by a probe type ultrasonicator to obtain a white translucent dispersion of MCA-modified vesicles. After kept standing at 50° C. for 2 hours, this liquid dispersion was subjected to measurement of the particle diameter of the vesicle with a particle distribution measurement apparatus. The average diameter was 41±19 nm.

The vesicles modified with 10 mol % MCA, and with 20 mol % MCA were prepared and subjected to particle size measurement in the same manner as above. The average particle diameters of the vesicles were 35±13 nm for the 10 mol % MCA-modified vesicle, and 36±10 nm for 20 mol % MCA-modified vesicle. Nearly the same diameters were obtained with 15 mol % MCA-modified vesicles and 25 mol % MCA-modified vesicles.

The dispersion stabilities of the MCA-modified vesicles modified with 5 mol %, 10 mol %, 15 mol %, 20 mol %, and 25 mol % MCA was evaluated by measuring the absorbance (turbidity) at 500 nm immediately after the preparation of the vesicle and after standing of the dispersion at 25° C. for 3 days. As the results, the increase of the turbidity by standing was varied depending on the amount of addition of MCA as follows: 5 mol %>10 mol %>15 mol %>20 mol % ≦25 mol %. The increase of the amount of the MCA addition suppresses the turbidity increase, and raises the stability of the vesicles.

The turbidity increase at 25° C. for three days immediately after the preparation of the 20 mol % MCA-modified vesicle dispersion was 15.6% relative to that of the unmodified DPPC vesicle dispersion taken as 100%. This shows that the modification of the vesicle by MCA stabilizes effectively the dispersion of the vesicles The above results are shown in Table 2 together with the results of Comparative Examples 7 to 11 described later. Table 2 shows the relative values of the turbidity increase of 5 wt % DPPC vesicle dispersions during standing at 25° C. for 3 days immediately after the preparation of the vesicle dispersions, where the turbidity increase rate (referred simply to as "increase rate" in Table 2) of unmodified vesicle dispersion is taken to be 100%. In Table 2, the numerals in the parentheses indicate the added amount of the modifier in mol %. The smaller value of the turbidity increase means the higher stability of the vesicle. Table 2 shows high usefulness of the vesicle stabilizer of the present invention, and the effectiveness is comparable with the satisfactory effect given by the oligosaccharides described later in Comparative Examples 1 and 2. The deviation of the data in Table 2 from the data in Table 1 is within the experimental error.

As shown above the vesicle stabilizer of the present invention exhibits excellent effect by increasing the amount of addition.

TABLE 2

| Modifier | Increase rate (%) |
|---|---|
| Unmodified | — | 100 |

TABLE 2-continued

| | Modifier | | | Increase rate (%) |
|---|---|---|---|---|
| (DPPC vesicle) | | | | |
| Present invention | | MCA | (5) | 47.8 |
| (Example 8) | | | (10) | 32.5 |
| | | | (15) | 19.9 |
| | | | (20) | 15.6 |
| | | | (25) | 17.2 |
| Comparative Example | | | | |
| 7 | Oligosaccharide derivative | MCPA | (5) | 10.3 |
| 8 | Oligosaccharide derivative | MPMP | (5) | 11.2 |
| 9 | Sucrose fatty acid ester | P-1695 | (5) | 65.4 |
| | | | (10) | 49.7 |
| | | | (15) | 30.5 |
| | | | (20) | 29.1 |
| 10 | Polyethylene glycol derivative | Nonion S-208 | (5) | 60.2 |
| | | | (10) | 45.2 |
| | | | (15) | 27.8 |
| | | | (20) | — |
| 11 | Polyethylene glycol derivative | Nonion S-215 | (5) | 39.8 |
| | | | (10) | 30.1 |
| | | | (15) | 23.0 |
| | | | (20) | — |

COMPARATIVE EXAMPLE 7

Maltopentaose cetylamide (hereinafter referred to as "MPCA") was introduced into a 5 wt % DPPC vesicle dispersion at a ratio of 5 mol % under the same conditions as in Example 8. The resulting MPCA-modified DPPC vesicles had an average particle diameter of 32±9 nm, and caused the turbidity increase of 12.7% of that of the unmodified DPPC vesicles.

COMPARATIVE EXAMPLE 8

Maltopentaose monopalmitate (hereinafter referred to as "MPMP") was introduced at a ratio of 5 mol % into a DPPC vesicle in the same manner as in Example 8. The resulting MPMP-modified DPPC vesicles had an average particle diameter of 34±12 nm, and caused the turbidity increase of as low as 11.2% of that of the unmodified DPPC vesicles. The stabilization of the vesicle dispersion was remarkable.

The above Comparative Examples 7 and 8 employ an oligosaccharide derivative as the modifier.

COMPARATIVE EXAMPLE 9

Comparative test was conducted by using as the DPPC vesicle modifier a sugar ester (P-1695, trade name, made by Mitsubishi Kasei Shokuhin K.K.) as a typical example of a sugar fatty acid ester at ratios of 5 mol %, 10 mol %, 15 mol %, and 20 mol %. In the modification with the sugar ester (P-1695), the resulting modified vesicles had an average particle diameter of 39±14 nm at the modifier addition ratio of 5 mol %, and 33±7 nm at the modifier addition rate of 20 mol %, the diameter not much depending on the modifier addition ratio. The modified vesicles caused the turbidity increase of 65.4% of that of the unmodified DPPC vesicles at the modifier addition ratio of 5 mol %, and 29.1% of that of the unmodified DPPC vesicles at the modifier addition ratio of 20 mol %, the increase of modifier ratio leading to higher stabilization.

COMPARATIVE EXAMPLE 10

Comparative test was conducted by using as the DPPC vesicle modifier a purified commercial polyethylene glycol monocetyl ether of ethylene glycol polymerization degree of 8 (Nonion S-208, trade name, made by Nippon Oil and Fats Co., Ltd.). The resulting modified vesicles had an average particle diameter of 42±15 nm at the modifier ratio of 5 mol %, and nearly the same average diameter at the modifier ratio of 15 mol %. The modified vesicles with the modifier of 5 mol % caused the turbidity increase of 60.2% of that of the unmodified DPPC vesicles. At the modifier ratio of 20 mol %, the vesicles collapsed, and neither the average diameter nor the turbidity increase could be measured.

COMPARATIVE EXAMPLE 11

Comparative test was conducted by using as the DPPC vesicle modifier a purified commercial polyethylene glycol monostearyl ether of ethylene glycol polymerization degree of 15 (Nonion S-215, trade name, made by Nippon Oil and Fats Co., Ltd.) at the same molar ratios as in Comparative Example 9. The resulting modified vesicles had an average particle diameter of 31±11 nm at the modifier ratio of 5 mol %, and 39±14 nm at the modifier ratio of 15 mol %. The average diameter not greatly affected by the modifier ratio. The modified vesicles at the modifier ratio of 5 mol % caused the turbidity increase of 39.8% of that of the unmodified DPPC vesicles. At the modifier ratio of 15 mol %, the turbidity increase was 23.0%, which was the minimum with this modifier. At the modifier ratio of 20 mol %, the vesicles collapsed as in Comparative Example 10, and neither the average diameter nor the turbidity increase could be measured.

EXAMPLE 9

From 100 mg of di-N-acetylchitobiose (hereinafter simply referred to as "chitobiose"), chitobiose lactone was prepared by lactonization in the same manner as in Example 8. This chitobiose lactone together with an equimolar amount of oleylamine were refluxed in methanol under a nitrogen atmosphere for 3 hours to obtain a crude product solution of di-N-acetylchitobiose oleylamine (hereinafter referred to as "DACOA").

The obtained DACOA solution was evaporated to dryness at 40° C. under a nitrogen atmosphere, and the residue was extracted with hexane by solid-liquid extraction to remove impurities into the hexane. The residue was dissolved in methanol, and purified by liquid chromatography to remove the unreacted matters. Thus the purified DACOA was obtained in a yield of 9.3 mg (overall yield: 9.1%).

In IR spectrometry of the purified DACOA, peaks were observed at about 2700 to about 3000 $cm^{-1}$ assigned to an alkyl chain, at about 700 $cm^{-1}$ assigned to out-of-plane bending vibration of CH—, at about 1650 $cm^{-1}$ assigned to C=O stretching vibration of the amide bond, and at about 1550 $cm^{-1}$ assigned to bending vibration of N-H. Accordingly, the obtained DACOA had an oleyl group linked through an amide bond to the anomer carbon of the reducing terminal group of chitobiose.

A powdery lipid mixture containing the above DACOA (DPPC:cholesterol:distearylphosphatidic acid:DACOA= 10:9:0.9:5 in molar ratio) was prepared by freeze-drying from benzene. To 250 mg of this freeze-dried mixture, 5 ml of saline was added, and the mixture was stirred at 4° C. for 12 hours. The resulting white turbid dispersion was treated with an extruder. In this extruder treatment, the dispersion was passed through filters of 1.0 μm, 0.4 μm, and 0.2 μm respectively five times sequentially. Thereby a white transparent DACOA-modified vesicle dispersion was obtained, which had an average particle diameter of 200 nm.

To this dispersion, calcium chloride (as calcium ion) was added to be 5 mM, and the viscosity of the dispersion was measured with a rotating viscometer (Vismetron VS-AK). The viscosity of 5 cp was not changed by addition of the calcium ion. On the contrary, the dispersion of the vesicles prepared from powdery lipid mixture not containing DACOA (DPPC:cholesterol:distearylphosphatidic acid= 10:9:0.9 in molar ratio) aggregated immediately on addition of calcium ion because of negative charge on the surface of the vesicle, causing the viscosity rise up to 11 cp.

EXAMPLE 10

From 7.0 g of cellobiose, cellobiose lactone was prepared by lactonization in the same manner as in Example 8. This cellobiose lactone together with an equimolar amount of distearoyl phosphatidyl ethanolamine dissolved in chloroform were treated in the same manner as in Example 8 to synthesize cellobiose distearoylphosphatidyl ethanolamine (herein after referred to "SDSPE").

The obtained SDSPE was extracted with hexane by solid-liquid extraction to remove impurities into the hexane. The SDSPE residue was dissolved in methanol, and purified by use of a silica gel column (mobile phase: mixed solvent of toluene with ethyl acetate) to obtain purified SDSPE in a yield of 5.2 g (overall yield: 24.8%).

In IR spectrometry of the purified product, a peak was observed at about 2700 to about 2900 $cm^{-1}$ assigned to the stearyl group, thereby the progress of the amidation reaction being confirmed.

10.0 g of a powdery lipid mixture containing the above purified SDSPE (hydrogenated lecithin: cholesterol:stearic acid:SDSPE=7:7:2:4 in molar ratio) was dispersed in 200 ml of saline, and the dispersion was stirred at 4° C. for 24 hours. The resulting dispersion was treated with a microfluidizer at 2500 psi at 4° C. for 15 minutes to obtain a dispersion of SDSPE-modified vesicles having average particle diameter of 350±95 nm. This dispersion was centrifuged (100000 G, 30 minutes) to obtain a precipitate of vesicles. The precipitate was dispersed again into a solution to be 5% by weight. Occurrence of aggregation of the vesicles was tested by adding dextran (molecular weight 40000) to the dispersion and measuring the turbidity change at 800 nm. The SDSPE-modified vesicles caused little rise of turbidity, whereas the unmodified vesicles caused rise of turbidity even at 1 wt % vesicle dispersion. Therefrom the modification was confirmed to be effective to inhibition of aggregation caused by dextran.

EXAMPLE 11

To 2.00 g of maltose, 15 ml of pyridine was added, and to the mixture 15 ml of acetic anhydride was added dropwise at 4° C. with stirring. Having been left standing at 4° C. for 12 hours, the reaction mixture was evaporated to dryness. The evaporated residue was recrystallized from 2-isopropanol, and dried in vacuo to obtain acetylated maltose. In the IR spectrum of the obtained product, a peak appeared at about 1750 $cm^{-1}$ assigned to C=O stretching vibration of the acetyl group, and the peak disappeared at about 3400 $cm^{-1}$ assigned to O-H stretching vibration, whereby all the hydroxyl groups in the saccharide skeleton was confirmed to have been acetylated. The acetylated maltose was obtained in a yield of 3.70 g (93.3%).

2.30 g of the above acetylated maltose and 2.00 g of distearyl glycerol were dissolved in 40 ml of 1,2-dichloroethane. Thereto, powdery molecular sieve was added, and further thereto, 2.1 g of trimethylsilyltrifluoromethane sulfonate was added gradually. After stirring for 20 hours the molecular sieve was removed, and the reaction product was isolated and purified by a silica gel column (solvent:toluene:ethyl acetate=3:1 by volume). In silica-gel thin layer chromatography (solvent:toluene:ethyl acetate=3:1 by volume), the product gave two spots: α-isomer at Rf 0.10, and β-isomer at Rf 0.29. The IR spectrum of the purified product shows absorption peaks of a long chain alkyl chain at about 2850 $cm^{-1}$ and at about 2900 $cm^{-1}$, which proves the bonding of the distearylglycerol to the acetylated maltose. The yield of the powdery product was 3.60 g (88.4%, α-isomer:1.30 g, β-isomer:2.30 g).

1.00 g of the α- or β-acetylated maltose distearylglycerol was dissolved in 20 ml of methanol, and thereto 2 ml respectively of triethylamine and pure water was added. The mixture was refluxed for 12 hours. The reaction product was crystallized from the methanol, and the crystalline product was dried in vacuo. The IR spectrum of the product in this stage showed disappearance of the absorption peak at about 1750 $cm^{-1}$ assigned to C=O stretching vibration of an acetyl group and appearance of an absorption peak at about 3400 $cm^{-1}$ assigned to O-H stretching vibration, which proves the complete hydrolysis of the acetyl groups.

The proton NMR spectrum of the product showed proton integral ratio of the protons of the alkyl groups at the β-carbon and the following carbons to the protons of the saccharide skeleton, glycerol, and —$OCH_2CH_2$ was 2.51 for the calculated value of 2.33, which proves the introduction of distearylglycerol to saccharide skeleton at a molar ratio of 1:1.

The carbon NMR spectrum showed the change of the chemical shift of the anomer carbon from 92 ppm of maltose to 103 ppm, which proves the selective bonding of distearyl glycerol to the anomer carbon.

The 1,2-di-octadecyl-O-α(β)-maltosyl-glycerol (hereinafter referred to as "DOMG") was obtained in a yield of 0.72 g (95.0%).

The modification of the surface of the vesicle was conducted as follows. 3.13 mg of the above DOMG was dissolved in 1 ml of chloroform. Thereto, a solution of 50 mg of dipalmitoyl phosphatidyl choline (DPPC) in 5 ml of chloroform was added, thereby DOMG being about 5 mol % relative to DPPC. With this mixture, a thin film was formed on an inside wall of an eggplant shape flask by means of a rotary evaporator. Thereto, 10 ml of pure water was added, and the mixture was agitated with glass beads by a vortex mixer to obtain a turbid dispersion of DOMG-modified vesicles. This dispersion was treated by use of an extruder (pore diameter of final passing filter: 0.05 μm) to obtain a vesicle dispersion having controlled particle diameter in the range of 35±15 nm.

Other DOMG-modified vesicle dispersions were prepared by use of 10 mol %, 15 mol %, and 20 mol % of DOMG relative to the DPPC otherwise in the same manner as above. The dispersions were left standing, and the change of the turbidity was monitored at 4° C. As the results, the increase of the turbidity was varied depending on the amount of the modified DOMG as follows: 5 mol %>10 mol %>15 mol %>20 The increase of the amount of the DOMG suppresses the turbidity increase rate, and raises the stability of the vesicles.

From the turbidity increase at 4° C. for 24 hours immediately after the preparation of the MCA-modified vesicle dispersion, the modification with 5 mol % DOMG was not so effective to the vesicle stabilization, whereas the 20% DOMG-modified vesicle dispersion gave the turbidity increase of 11.2% relative to that of the unmodified DPPC vesicle dispersion taken as 100%. Thereby it was confirmed that the modification of the vesicle by DOMG stabilizes effectively the dispersion of the vesicles.

The above results are shown in Table 3 together with the results of Comparative Examples 12 to 16 described later. Table 3 shows the relative values of the turbidity increase of 5% DPPC vesicle dispersions by weight during standing at 4° C. for 24 hours immediately after the preparation of the vesicle dispersions, where the turbidity increase rate (referred simply to as "increase rate" in Table 3) of unmodified vesicle dispersion is taken to be 100 %. In Table 3, the numerals in the parentheses indicate the added amount of the modifier in mol %. The smaller value of turbidity increase means the higher stability of the vesicle. Table 3 shows high usefulness of the vesicle stabilizer of the present invention, and the effectiveness is comparable with the satisfactory effect given by the oligosaccharides described later in Comparative Examples 1 and 2. The deviation of the data in Table 3 from the data in Tables 1 and 2 is within the experimental error.

As shown above the vesicle stabilizer of the present invention exhibits more excellent effect by increasing the amount of addition.

TABLE 3

| | Modifier | | | Increase rate (%) |
|---|---|---|---|---|
| Unmodified (DPPC vesicle) | — | | | 100 |
| Present invention (Example 11) | DOMG | | (5) | 45.5 |
| | | | (10) | 28.9 |
| | | | (15) | 16.0 |
| | | | (20) | 11.2 |
| Comparative Example | | | | |
| 12 | Oligosaccharide derivative | DOMPG | (5) | 12.1 |
| 13 | Oligosaccharide derivative | MPMP | (5) | 13.5 |
| 14 | Sucrose fatty acid ester | P-1695 | (5) | 67.2 |
| | | | (10) | 52.4 |
| | | | (15) | 33.8 |
| | | | (20) | 32.5 |
| 15 | Polyethylene glycol derivative | Nonion S-208 | (5) | 62.7 |
| | | | (10) | 49.0 |
| | | | (15) | 30.1 |
| | | | (20) | — |
| 16 | Polyethylene glycol derivative | Nonion S-215 | (5) | 43.2 |
| | | | (10) | 34.1 |
| | | | (15) | 29.3 |
| | | | (20) | — |

COMPARATIVE EXAMPLE 12

Dioctadecylmaltopentaosyl glycerol (hereinafter referred to as "DOMPG") was introduced into a 5 wt % DPPC vesicle at a ratio of 5 mol % under the same conditions as in the DOMG-modified vesicle preparation on Example 11. The resulting DOMPG-modified DPPC vesicle caused the turbidity increase of 12.1% of that of the unmodified DPPC vesicle.

COMPARATIVE EXAMPLE 13

Maltopentaose monopalmitate (hereinafter referred to as "MPMP") was introduced at a ratio of 5 mol % into a DPPC vesicle in the same manner as in Comparative Example 12. The resulting MPMP-modified DPPC vesicles caused the turbidity increase of 13.5% of that of the unmodified DPPC vesicles.

COMPARATIVE EXAMPLE 14

Comparative test was conducted by using as the DPPC vesicle modifier a sugar ester (P-1695, trade name, made by Mitsubishi Kasei Shokuhin K.K.) as a sugar fatty acid ester at ratios of 5 mol %, 10 mol %, 15 mol %, and 20 mol %. The modified vesicles caused the turbidity increase of 32.5% of that of the unmodified DPPC vesicles even at the modifier addition ratio of 20 mol %, the aggregation inhibition effect being insufficient.

COMPARATIVE EXAMPLE 15

Comparative test was conducted by using as the DPPC vesicle modifier a commercial polyethylene glycol monocetyl ether of ethylene glycol polymerization degree of 8 (Nonion S-208, trade name, made by Nippon Oil and Fats Co., Ltd.). The vesicles modified with the modifier of 15 mol % caused the turbidity increase of 30.1% of that of the unmodified DPPC vesicles. At the modifier ratio higher than 15 mol %, the vesicles collapsed, and the turbidity decreased rapidly.

COMPARATIVE EXAMPLE 16

Comparative test was conducted by using as the DPPC vesicle modifier a purified commercial polyethylene glycol monostearyl ether of ethylene glycol polymerization degree of 15 (Nonion S-215, trade name, made by Nippon Oil and Fats Co., Ltd.). The modified vesicles at the modifier ratio of 15 mol % caused the turbidity increase of 29.3% of that of the unmodified DPPC vesicles. At the modifier ratio of 20 mol %, the vesicles collapsed, and the turbidity measurement turned to meaningless.

EXAMPLE 12

2.4 mg of DOMG prepared in the same manner as in Example 11 was dissolved in 1 ml of chloroform. This solution was mixed with a solution of 100 mg of DPPC in 5 ml of chloroform, thereby DOMG being 2 mol % of DPPC. The solution mixture was evaporated by means of an evaporator to form a thin film on the inside wall of an eggplant-shape flask. Then 10 ml of pure water was added thereto so as to obtain a concentration of 1.0% by weight of the vesicles. The mixture was stirred with glass beads by means of a vortex mixer, and subsequently treated by an extruder to prepare a dispersion of DOMG-modified DPPC vesicles having controlled diameters of particles. A portion of the resulting dispersion was diluted to a fivefold volume with pure water to prepare a dispersion having vesicle concentration of 0.2% by weight.

The two dispersions of the DOMG-modified vesicles having concentrations of 1.0% by weight and 0.2% by weight were left standing at 4° C. for 24 hours, and were ultracentrifuged (300000 G, 60 minutes). The free DOMG in the supernatant was determined by a phenol-sulfuric acid method, and therefrom the ratio of introduction DOMG to the vesicles was calculated.

As the results, the introduction ratios were 94.3%, and 77.0% respectively at the vesicle concentrations of 1.0% by weight and 0.2% by weight. The results are shown in Table 4 together with the results of Comparative Examples 6 and 7 described later in which an oligosaccharide derivative was employed. In Table 4, the introduction ratio (%) shows the ratio of the modifier introduced into the vesicle to the added modifier. The higher introduction ratio means the more stable fixation of the modifier in the bimolecular membrane of the vesicle.

TABLE 4

| Vesicle concentration (wt %) | 1.0 | 0.2 |
|---|---|---|
| Modifier | Introduction ratio (%) | |
| Invention (Example 12) | 94.3 | 77.0 |
| Comparative example 17 MPMP | 75.8 | 48.5 |
| Comparative example 18 DOMPG | 83.2 | 70.9 |

COMPARATIVE EXAMPLE 17

MPMP was introduced at a ratio of 2 mol % into 1.0 wt % DPPC vesicle dispersion under the same conditions as in the above Example 12, and the introduction ratios of the MPMP were determined. The introduction ratio was low in comparison with that of DOMG, the stabilizer of the present invention, in the DOMG-modified DPPC vesicles.

COMPARATIVE EXAMPLE 18

DOMPG was introduced at a ratio of 2 mol % into 1.0 wt % DPPC vesicle dispersion in the same manner as in Comparative Example 17. The introduction ratio was low in comparison with that of DOMG, the stabilizer of the present invention, in the DOMG-modified DPPC vesicles.

EXAMPLE 13

From 5.0 g of cellobiose, acetylated cellobiose was prepared by acetylation in the same manner as in Example 11. The obtained acetylated cellobiose was mixed with equimolar amount of tetraethyleneglycosyl cholesterol which is a cholesterol bonded with tetraethylene glycol through an ether linkage. From the mixture, cellobiosyl tetraethyleneglycosyl cholesterol (hereinafter referred to as "STEC") was synthesized according to the method of Example 11 in yield of 5.8 g (overall yield: 44.8%). The IR spectrum of the resulting STEC showed an absorption peak at 2700 to 2900 $cm^{-1}$ coming from tetraethylene glycol. The carbon NMR spectrum of the STEC showed the change of the chemical shift of the anomer carbon from 92 ppm to 104 ppm. Thereby the selective bonding of the tetraethyleneglycosyl cholesterol to the anomer carbon of the cellobiose was confirmed.

5.0 g of a powdery lipid mixture containing the above STEC (DPPC:cholesterol:stearic acid:STEC=7:7:2:2 in molar ratio) was dispersed in 100 ml of saline, and the dispersion was stirred at 4° C. for 24 hours. The resulting dispersion was treated with a microfluidizer at 2500 psi at 4° C. for 15 minutes. This dispersion was centrifuged (10000 G, 30 minutes) to obtain precipitate of STEC-modified vesicles. The precipitate was dispersed again in to saline to be 5 wt %. The stability of the vesicles was evaluated by adding 2.5 wt % solution of dextran (molecular weight 40000) to the above vesicle layer and measuring the turbidity change at 800 nm. The STEC-modified vesicles caused the turbidity increase of 58% of that of the unmodified vesicles (DPPC:cholesterol:stearic acid=7:7:2 in molar ratio), thereby the inhibition effect of STEC, a vesicle stabilizer of the present invention being confirmed.

EXAMPLE 14

Acetylated lactose derived from 5.0 g of lactose was mixed with an equimolar amount of dioctadecyl glycerol. Therefrom, dioctadecyl lactosyl glycerol (hereinafter referred to as "DOLG") was synthesized according to the method in Example 1 in a yield of 8.9 g (overall yield: 64.5%). The carbon NMR of the resulting DOLG showed the change of the chemical shift of the anomer carbon from 92 ppm to 104 ppm, thereby the selective bonding of the dioctadecyl glycerol to the anomer carbon of the lactose being confirmed.

5 g of a powdery lipid mixture containing the above DOLG (DPPC:cholesterol:stearic acid:DOLG=7:7:2:2 in molar ratio) was dispersed in 100 ml of saline. The dispersion was agitated with glass beads by means of a vortex mixer to prepare a DOLG-modified vesicle dispersion. Then the particle diameter was adjusted by use of an extruder.

The stability of the dispersion of the DOLG-modified vesicles having adjusted particle diameters was evaluated by addition of 5 mM calcium chloride and observing the viscosity change. The viscosity was measured at 37° C. by a rotating viscometer. The viscosity was kept at 5 cp at shear rate of 1.15 $sec^{-1}$ without viscosity increase by addition of calcium chloride. On the contrary, a dispersion of unmodified vesicles prepared from a powdery lipid mixture containing no DOLG (DPPC:cholesterol:stearic acid=7:7:2 in molar ratio) caused immediate aggregation of the vesicles on addition of calcium ion in the same manner as above because of the negative charge on the surface of the vesicle, and the viscosity increased up to 11 cp. Accordingly, the sufficient effect of the DOLG, a vesicle stabilizer of the present invention, was confirmed in inhibiting the aggregation of vesicles by calcium ion.

EXAMPLE 15

Polymerizable 2,4-octadecadienyl-0-α(β)-maltose (hereinafter referred to as "ODM") was prepared from maltose and 2,4-octadecadienol according to the method shown in Example 11. A solution of 2.0 mg of this ODM in 1 ml of chloroform was mixed with a solution of 200 mg of di(2, 4-octadecadienoyl)phosphatidylcholine (hereinafter referred to as "DODPC") as a polymerizable lipid in 5 ml of chloroform. The mixture was evaporated by a rotary evaporator to form a thin film on a wall of an eggplant-shape flask. 20 ml of pure water was added thereto, and agitated with glass beads by a vortex mixer. The resulting ODM-modified vesicle dispersion was treated by an extruder to prepare a dispersion of nearly uniform particle diameters. The vesicle dispersion was irradiated with γ-ray to copolymerize the ODM and the polymerizable lipid, DODPC. A portion of the irradiated dispersion was diluted fivefold with pure water and was left standing at 4° C. for 24 hours. The introduction ratio of ODM was measured by centrifuging the diluted and undiluted dispersions (300000 G, 60 minutes) respectively and determining the ODM in the supernatant by a phenol-sulfuric acid method. The introduction ratio was as high as 94.2% in the both diluted and undiluted dispersions without lowering of the introduction ratio by dilution.

In the system in which ODM was not copolymerized, the introduction ratio of ODM to the vesicle was decreased from 93.8% to 66.9% by fivefold dilution of the vesicle dispersion.

The above vesicle dispersion before the fivefold dilution was left standing at 4° C. for 24 hours exhibited turbidity increase of as low as 10.9% of that of the unmodified vesicles. Thereby it was confirmed that the copolymerization of ODM, a vesicle stabilizer of the present invention, with vesicle is highly effective in stabilization of the vesicle.

The oligosaccharide derivative of the present invention, when used as a modifier of lipid vesicles, is highly effective in stabilizing a dispersion of lipid vesicles. This derivative is commercially advantageous in synthesis efficiency and modification effects in comparison with conventional oligosaccharide fatty acid esters.

The vesicle stabilizer of the present invention, when used as a modifier of lipid vesicles, not only inhibits the aggregation of the phospholipid vesicle and stabilizes a dispersion of the vesicles in a solution of protein or the like, but also is capable of inhibiting phagocytosis in a living body. Accordingly, the vesicle stabilizer of the present invention is promising in stabilizing vesicles as a drug delivery system in a living body.

What is claimed is:

1. A stabilized phospholipid vesible comprising a phospholipid vesicle having membrane constituents and at least 0.01 mol % based on the membrane constituents of the phospholipid vesicle of an oligosaccharide lipid having 2 to 20 saccharide units and having a hydrophobic group linked through an amide linkage to an anomer carbon at a reducing end group constituted of an aldose.

2. The stabilized phospholipid vesicle of claim 1 wherein the hydrophobic group is derived from a compound which has an amino group and an alkyl group of 12 to 22 carbons.

3. The stabilized phospholipid vesicle of claim 1 wherein the hydrophobic group is derived from a compound which has an amino group and an aliphatic hydrocarbon group of 12 to 22 carbons having 1 to 4 unsaturated bonds.

4. A stabilized phospholipid vesicle comprising a phospholipid vesicle having membrane constituents and at least 0.01 mol % based on the membrane constituents of the phospholipid vesicle of an oligasaccharide lipid having 2 to 20 saccharide units and having a hydrophobic group linked through an ether linkage to an anomer carbon at a reducing end group constituted of an aldose.

5. The stabilized phospholipid vesicle of claim 4 wherein the hydrophobic group is derived from a compound which has a hydroxyl group and an alkyl group of 12 to 22 carbons.

6. The stabilized phospholipid vesicle of claim 4 wherein the hydrophobic group is derived from a compound which has a hydroxyl group and an aliphatic hydrocarbon group of 12 to 22 carbons having 1 to 4 unsaturated bonds.

* * * * *